United States Patent [19]

Kragten et al.

[11] Patent Number: 5,859,301

[45] Date of Patent: Jan. 12, 1999

[54] PROCESS FOR PREPARING ALKANONES AND ALKANOLS

[75] Inventors: Ubaldus F. Kragten, Beek; Henricus A. C. Baur, Herten, both of Netherlands

[73] Assignee: DSM N.V., Heerlen, Netherlands

[21] Appl. No.: 363,238

[22] Filed: Dec. 23, 1994

[30] Foreign Application Priority Data

Dec. 23, 1993 [BE] Belgium .................................. 93 01446

[51] Int. Cl.$^6$ .................................................. C07C 45/53
[52] U.S. Cl. ......................... 568/342; 568/389; 568/311
[58] Field of Search .................................... 568/311, 342, 568/389

[56] References Cited

U.S. PATENT DOCUMENTS

| | | | |
|---|---|---|---|
| 2,851,496 | 9/1958 | Cates et al. | 568/342 |
| 4,042,630 | 8/1977 | Wolters et al. | 568/342 |
| 4,238,415 | 12/1980 | Bryan | 568/342 |
| 4,543,427 | 9/1985 | Hartig et al. | 568/342 |
| 5,206,441 | 4/1993 | Reimer | 568/342 |

FOREIGN PATENT DOCUMENTS

| | | | |
|---|---|---|---|
| 0004105 | 9/1979 | European Pat. Off. | 568/342 |
| 0092867 | 11/1983 | European Pat. Off. | 568/342 |
| 0096798 | 12/1983 | European Pat. Off. | 568/342 |
| 0554944 | 8/1993 | European Pat. Off. | 568/342 |
| 1369732 | 12/1964 | France | 568/342 |
| 1382849 | 2/1975 | United Kingdom | 568/342 |
| 1398293 | 6/1975 | United Kingdom | 568/342 |
| 9216487 | 10/1992 | WIPO | 568/342 |

*Primary Examiner*—James H. Reamer
*Assistant Examiner*—J. Reamer
*Attorney, Agent, or Firm*—Cushman Darby & Cushman IP Group of Pillsbury Madison & Sutro, LLP

[57] ABSTRACT

An improved process for preparing alkanones and alkanols by oxidizing an alkane and/or alkene having from 3 to 30 carbon atoms to form an oxidation mixture containing alkylhydroperoxide. A basic, aqueous solution is added to the oxidation mixture so that a separate basic water phase with a pH higher than 8.5 is formed. The alkylhydroperoxide is then decomposed in the presence of a heterogeneous catalyst which contains a metal compound immobilized on a carrier material. The metal of the catalyst is selected from the group consisting of Mn, Fe, Co, Ni, and Cu. The carrier material is stable in the presence of the separate basic water phase.

19 Claims, 1 Drawing Sheet

PROCESS FOR PREPARING ALKANONES AND ALKANOLS

BACKGROUND OF THE INVENTION

1. Field of Invention

The present invention pertains to an improved process for preparing alkanones and alkanols. In particular, the present invention involves the steps of oxidizing an alkane and/or alkene having from 3 to 30 carbon atoms to form an oxidation mixture containing alkylhydroperoxide, adding a basic aqueous solution to the oxidation mixture, and decomposing the alkylhydroperoxide in the presence of a heterogeneous decomposition catalyst.

2. Description of Related Art

A process for preparing cyclohexanone and cyclohexanol is described in U.S. Pat. No. 4,543,427 issued to Hartig et al. According to the Hartig patent, cyclohexane is first oxidized with air or oxygen to produce an oxidation mixture containing cyclohexyl hydroperoxide. The cyclohexyl hydroperoxide is subsequently decomposed into cyclohexanone and cyclohexanol. The decomposition is effected in the presence of a heterogeneous decomposition catalyst consisting of cobalt immobilized on a zeolite carrier. This decomposition catalyst is said to have a longer life and greater resistance to acids and water than metal-on-carrier catalysts known in the art, such as cobalt on active aluminum oxide, silica gel, or carbon, as described in U.S. Pat. No. 2,851,496 issued to Cates et al.

One disadvantage of the above-mentioned process is that it employs a zeolite as carrier material. Unfortunately, the zeolite is very difficult to obtain. Another disadvantage is that a decrease in the catalyst activity is generally observed. That is, a small amount of cobalt from the cobalt-on-zeolite decomposition catalyst dissolves in the reaction mixture, resulting in limited catalyst life. A further disadvantage is that the presence of a separate water phase during the decomposition of the alkylhydroperoxides further diminishes the catalyst activity by encouraging the cobalt to dissolve in the reaction mixture. The separate water phase thereby causes a significant decrease in the activity of the decomposition catalyst over a short period of time (e.g., a few hours). The separate water phase forms as a byproduct in the oxidation reaction of the cyclohexane and in the decomposition reaction. The negative effect of a separate water phase on the life of a heterogeneous decomposition catalyst is also described in, for instance, U.S. Pat. No. 4,042,630 issued to Wolters et al.

Wolters et al. purports to overcome the problems associated with the Hartig patent by providing a process wherein the formation of a separate water phase is prevented during the decomposition of a cycloalkylhydroperoxide by continuously stripping the oxidation mixture with a stripping gas. The water concentration is preferably maintained at or below a saturation concentration. This stripping process, however, exhibits several distinct disadvantages. First, the stripping process requires a complex decomposition reactor for enabling decomposition and stripping to occur simultaneously and an elaborate apparatus for recirculating the stripping gas. In addition, the effect of the stripping step is not isolated to removing unwanted water. Instead, cyclohexane and reaction products such as cyclohexanol and cyclohexanone are undesirably stripped from the oxidation mixture by the stripping gas. Costly additional processing steps are often required to recover these valuable compounds.

SUMMARY OF THE INVENTION

Accordingly, it is an object of the present invention to provide a process wherein a readily available decomposition catalyst is employed to produce a high yield and selectivity of alkanones and alkanols.

It is a further object of the present invention to provide a process wherein a stable decomposition catalyst retains its activity and selectivity, even in the presence of water in the oxidation mixture.

It is still another object of the present invention to provide a process that obviates the need for stripping and removing water from the oxidation mixture before or during the decomposition of the alkylhydroperoxides.

The present invention achieves these objectives and overcomes the aforementioned problems associated with the prior art in that an amount of a basic, aqueous solution is present in the oxidation mixture so that a separate water phase with a pH higher than 8.5 is present during the decomposition step. The catalyst includes a metal that is preferably selected from the group comprising Mn, Fe, Co, Ni, and Cu, and a carrier material that is stable in the presence of the separate basic water phase.

The inventors of the present invention have found that the decomposition catalyst exhibits a superior longevity when the decomposition step is effected using the process provided by the present invention. It has also been found that the present invention achieves the additional advantage of encouraging the decomposition of the alkylhydroperoxide to proceed more rapidly. Another feature of the present invention is that a high ratio of alkanone to alkanol product is achieved. This is particularly advantageous in instances where alkanone is the desired end product. Finally, the process of the present invention obviates the need to remove water from the oxidation mixture before or during the decomposition of the alkylhydroperoxide.

BRIEF DESCRIPTION OF THE DRAWINGS

The accompanying drawings illustrate the present invention. In such drawings.

DESCRIPTION OF THE PREFERRED EMBODIMENTS

Figure 1:
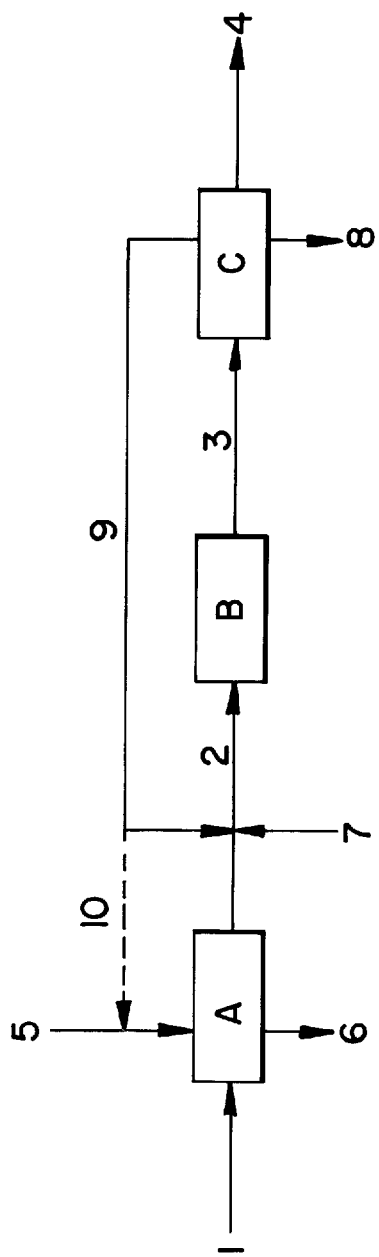
FIG. 1 is a schematic view representing a suitable process configuration for practicing the present invention according to a first preferred embodiment.

The present invention provides a process for producing alkanones and alkanols generally involves the following steps. First, an alkane and/or alkene, preferably having from 3 to 30 carbon atoms, is oxidized in a liquid phase in a manner generally known in the art to form an oxidation mixture containing alkylhydroperoxide. A basic, aqueous solution is added to the oxidation mixture so that a separate water phase having a pH higher than 8.5 is present. The alkylhydroperoxide intermediate is subsequently subjected to a decomposition step in the presence of a catalyst to form the alkanone (K) and alkanol (A) products. The decomposition catalyst generally includes a metal preferably selected from the group consisting of Mn, Fe, Co, Ni, and Cu and a carrier material that is stable in the presence of the separate basic water phase. It has been found that by effecting the decomposition of alkylhydroperoxide in a water phase with a pH higher than 8.5, a higher yield of alkanones and alkanols is achieved.

The oxidation step is accomplished by using, by way of example, air, pure oxygen, or a mixture of oxygen and an inert gas. Oxidation typically occurs at temperatures in the range of about 120° C. to about 200° C., and preferably at temperatures in the range of about 140° C. to about 180° C. The pressure at which the oxidation step occurs is not critical, and usually is set between 0.4 MPa and 5.0 MPa (i.e., 4 and 50 bar). The oxidation reaction usually requires a reaction time between 0.1 and 24 hours, and preferably at least 0.5 hours. In accordance with the above parameters, approximately 1 to 50 percent of the alkane undergoes conversion, although the conversion rate usually ranges from 1 to 25 percent.

Illustrative of the $C_3$–$C_{30}$ alkanes/alkenes which are useful as reactants in accordance with the present invention are, by way of example, propane, 2-methylpropane, cycloheptane, cyclohexane, cyclooctane, cyclododecane, methylbenzene, ethylbenzene, 2-propylbenzene, phenylcyclohexane, cyclohexene, diphenylmethane, phenylcyclododecane, 4-tertbutyl-1-cycloheptylbenzene, 2-isopropylnaphthalene, fluorene, 1,8-dimethylfluorene, and 1,2-dicyclohexylmethane. As shown by the above examples, the alkane may be branched, linear and/or cyclic. In addition, the alkane and/or alkene may have aromatic groups (e.g., benzene, phenol, naphthalene) and ethylenically unsaturated groups attached thereto.

The process is particularly efficacious for oxidizing cycloalkanes having from 4 to 18 carbon atoms, and especially for oxidizing cycloalkanes having from 6 to 12 carbon atoms (e.g., cyclohexane, cyclooctane and cyclododecane). The reaction products from the cyclohexane oxidation are especially useful in either the preparation of caprolactam (for nylon 6) or for the preparation of adipic acid (for nylon 6,6). The cyclohexanol and cyclohexanone thus obtained have been found to be pure enough, without further treatment, for further conversion into starting materials for the preparation of caprolactam.

The alkane and/or alkene is preferably oxidized in the absence of oxidation catalysts that tend to promote the decomposition of the alkylhydroperoxide formed. Therefore it is preferred that the reactor used for the oxidation step have an inert inner wall (e.g., an inner wall constructed of passivated steel, aluminum, glass, enamel, or equivalent material). The decomposition of the alkylhydroperoxide during oxidation is undesirable because of the elevated oxidation temperature. Decomposition at the oxidation temperature produces a higher yield of unwanted by-products. On the other hand, if the use of an oxidation catalyst is opted for, such catalysts generally include compounds of transition metals. The amount of transition metal should preferably be very small, in the order of from 0.1 to 10 parts by weight per million. Examples of such transition metals include cobalt, chromium, manganese, iron, nickel, copper, or mixtures thereof. Cobalt naphthenate and cobalt 2-ethylhexanate have been found to be suitable catalysts.

In addition to alkylhydroperoxide and a water phase, the oxidation mixture further typically includes small amounts of alkanol and alkanone product, as well as by-products such as esters and carboxylic acids.

After the oxidation step is completed, a neutralization step can optionally be performed on the oxidation mixture. According to the neutralization step, at least a portion of the acids contained in the oxidation mixture are neutralized by a neutralizing agent to thereby form a neutralized organic phase containing the alkylhyroperoxide. Preferably, a basic aqueous solution of a hydroxide or carbonate of an alkali metal, as described below, is used. The neutralization step may take place of a wide range of temperature, for instance from about 80° C. to about 170° C. Upon neutralization, a portion of the water phase can be separated and carried off, if desired.

Before the decomposition of the alkylhydroperoxide, the oxidation mixture is treated with the basic aqueous solution. The basic aqueous solution may be any aqueous solution that causes a separate water phase to form in the oxidation mixture which has a pH higher than 8.5 and is inert with respect to the catalyst. In general, ammoniacal aqueous solutions and aqueous solutions which contain amines are not inert with respect to the catalyst provided by the present invention and thus are less suited for use in the present invention. The basic aqueous solution preferably contains a dissolved amount of alkali metal hydroxide, alkali metal carbonate, alkali metal phosphate, or a combination thereof. Examples of useful and readily available alkali metals include, among others, sodium and potassium.

It is preferred to use an aqueous solution in which alkali metal hydroxide and alkali metal carbonate are dissolved inasmuch as these compounds can be recirculated in a manner such as that described in British Patent No. 1,398,293, the disclosure of which is incorporated herein by reference. According to this process, the aqueous phase containing the alkali metal hydroxide or alkali metal carbonate is extracted after the decomposition step and subsequently combusted in the presence of excess oxygen at a temperature of 550°–1200° C. The direct combustion of the extract provides sufficient heat to vaporize the water, yielding a combustion residue of solid alkali metal carbonate. The alkali metal carbonate so obtained can be dissolved in water and used anew as the basic aqueous solution according to the present invention. The solid alkali metal carbonate may optionally be hydrolyzed to an alkali metal hydroxide, which compound may also be used in the preparation of the basic aqueous solution according to the present invention. Preferably, the alkali solution has metal carbonate dissolved therein inasmuch as the aforementioned hydrolysis to the alkali metal hydroxide can thereby be omitted.

A portion of the basic aqueous solution will preferably consist of a recycled water phase which has been separated out after the decomposition. By recycling a portion of the water phase, a large amount of water phase can be created while the consumption of basic aqueous solution remains limited. The ratio of the returned amount of water phase and the amount of water phase eventually discharged may be between 50 and 0.

According to the invention, the pH of the separate water phase (measured at 25° C.) is higher than 8.5. More preferably, the pH is higher than 9.5 and most preferably higher than 10. Where an aqueous alkali metal carbonate solution is employed, the pH will be lower than 11. It has been found that, if the pH is any higher, extremely little metal compound dissolves in the oxidation mixture and the water phase.

The weight ratio between the oxidation mixture and the water phase during the decomposition of the alkylhydroperoxide is preferably between 200:1 and 1:20, and more preferably between 100:1 and 1:1. It has been found that if a relatively higher proportion of the water phase is present during the decomposition, the reaction rate of the decomposition will increase.

In the decomposition step of the present invention, alkylhydroperoxide is converted to alkanone and alkanol products by both the direct conversion thereof in the presence of a catalyst system and by the reaction between the alkylhydroperoxide and unreacted alkane. This "alkane participation" reaction plays an important role in determining the overall yield and the alkanone to alkanol (K/A) ratio.

The decomposition of the alkylhydroperoxide in the oxidation mixture is effected with the aid of a catalyst system in accordance with the present invention. The decomposition catalyst of the present invention includes a metal compound which is immobilized on a carrier material. The metal-containing compound preferably is a metal oxide compound. Examples of metal oxide compounds include the respective metal oxides of manganese (Mn), iron (Fe), cobalt (Co), nickel (Ni), and copper (Cu). It has been found that metals that form a stable anion complex (e.g., chromium (Cr)) are less suited for application in the process of the present invention. The carrier material is preferably stable in the presence of a separate water phase having pH higher than 8.5.

The metal oxide may be applied to the carrier by any of several processes known to those skilled in the art. For example, the catalysts may be prepared in a single step starting from readily available starting materials by applying impregnation and deposition-precipitation methods. Such methods are described in, for instance, J. W. Geus, *Preparation of Catalysts III*, 16 Studies in Surface Science & Catalysis 1–33 (Elsevier 1983) and P. J. v. d. Brink, A. Scholten, A. v. Wageningen, M. D. A. Lamers, A. J. v. Dillen, J. W. Geus, *Preparation of Catalysts V*, 63 Studies in Surface Science & Catalysis 527–536 (Elsevier 1991), the disclosures of which are incorporated herein by reference. A metal compound, which need not necessarily be the metal oxide, can be dissolved in a suitable solvent such as water and subsequently contacted with and deposited on the carrier. Next, the carrier is calcined, at an elevated temperature, such as preferably higher than 500° C., to form the metal oxide. Examples of suitable metal compounds include water-soluble metal compounds such as $Co(OH)_2$, $Co(OH)_3$, $CuO$, $Cu_2O$, $Fe_2O_3$, $CoO_x \cdot yH_2O$, $CuO_x \cdot yH_2O$, $FeO_x \cdot yH_2O$, $MnO_x \cdot yH_2O$ and $NiO_x \cdot yH_2O$, where x may equal ½, 1, 1½, 2, or 3, and where y may have a value of from 0 to 20.

The carrier material can be any organic or inorganic carrier material, so long as it is stable in the presence of a separate water phase having a pH higher than 8.5. Stable carrier material is herein defined to include materials that will barely dissolve, if at all, in the reaction mixture during the decomposition. Preferably, the carrier material is an inorganic carrier material. In particular, the carrier material preferably has a hydrophilic surface so that a water layer will readily form around the catalyst during the decomposition step. Exemplary carrier materials include, among others, silica, molecular sieves, $SnO_2$, $TiO_2$, $ZrO_2$, $MnO_2$, and carbon (e.g. charcoal), and the like. The carrier materials may have various shapes, including for example spherical, saddle, extrudated or tablet shapes. Various modified types of carrier materials may also be used, for instance, microporous and macroporous carriers.

Another class of decomposition catalysts useful in the present invention are catalysts that are based on Mn, Fe, Co, Ni, and Cu with $TiO_2$ or $ZrO_2$ as carrier material to which a ligand is attached, wherein the catalyst is at least essentially free of Si-O compounds. The metal compound and the ligands form a complex so that the metal compounds remain immobilized on the carrier material.

The ligands can be exemplified by groups represented by formula (A):

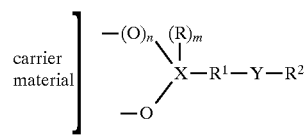

wherein:

n represents 0, 1, 2, m represents 0, 1, 2, wherein n+m=2,

X represents Ti or Zr,

R represents H or $C_{1-12}$ alkyl or alkoxy, $R^1$ represents $C_{2-6}$ alkyl,

Y represents S or $NR^3$, $R^2$ represents H or $R^4$—$NH^2$, wherein $R^4$ is $C_2$–$C_3$ alkyl, and $R^3$ represents H or $C_1$–$C_6$.

In addition, $R^1$ may contain ether groups and $R^2$, $R^3$ and $R^4$ may additionally contain 1 or 2 ether, alcohol or carboxyl groups.

The various R, $R^1$, $R^2$, $R^3$ and $R^4$ moieties can, although consistent with their respective definitions stated hereinabove, be linear, branched, cyclic or aromatic as the case may be. Again consistent with their respective definitions, R, $R^1$, $R^2$, $R^3$ and $R^4$ can be selected, as appropriate, from among linear alkyls, such as methyl, ethyl, propyl, butyl, pentyl, hexyl, heptyl, octyl, nonyl, decyl, undecyl, or dodecyl; branched alkyls, such as 2-methyl-propyl, 2-methyl-butyl, 2-methyl-pentyl, 3-methyl-pentyl, 2-methyl-hexyl, 3-methyl-hexyl, 2-methyl-heptyl, 3-methyl-heptyl, 4-methyl-heptyl, 2-dimethyl-ethyl, 2-dimethyl-propyl, 2-dimethyl-butyl, 2,3-dimethyl-butyl, 2-ethyl-pentyl, 3-ethyl-pentyl, 2-ethyl-hexyl, or 3-ethyl-hexyl; cyclic alkyls, such as cyclo-pentyl, cyclo-hexyl, cyclo-heptyl, cyclo-octyl, cyclo-dodecyl, methyl-cyclopentyl, methyl-cyclohexyl, methyl-cyclo-octyl, or methyl-cyclododecyl; or aromatic groups, such as phenyl, 2-methyl-phenyl, 2,6-dimethyl-phenyl, 2-ethyl-phenyl, 2,6-diethyl-phenyl, 2-isopropyl-phenyl, 2,6-diisopropyl-phenyl, 2-t.butyl-phenyl, naphtyl, 2-methyl-naphtyl, or 2,6-dimethyl-naphthyl. As indicated hereinabove with the formula (A) of an exemplary ligand, alkoxy-variants of the aforementioned can also be considered such as, for instance, when the R moiety is $C_1$–$C_{12}$ alkoxy the alkoxy variants are non-aromatic.

A disadvantage associated with these catalysts, however, is that a plurality of steps and starting materials are required to prepare these catalysts. In addition, these catalysts are less readily available. Accordingly, it is preferred to use a carrier material without ligands, with the metal compound being directly linked to the carrier material. Such catalysts can generally be prepared in a single step using starting materials that are readily available. A further disadvantage of using a catalyst having a carrier material to which a ligand is attached is that relatively less alkanone is produced during the decomposition. Still another disadvantage is that the rate of the decomposition reaction is lower than when the catalyst using a carrier material without ligands is used.

In general, the weight percentage of metal in relation to the carrier material (referring to the metal only) is between 0.05 and 8 wt. %. Preferably, the weight percentage is higher than 0.2 and lower than 4 wt. %.

Still another class of suitable decomposition catalysts are the metal oxides and the metal carbonates of Mn, Fe, Co, Ni and Cu. This class of catalysts is characterized in that the metal compound and the carrier material are identical.

Another suitable decomposition catalyst is an all-metal catalyst having a thin layer of a corresponding metal oxide deposited on its peripheral surface. An all-metal catalyst means a solid structure in the form of a solid catalyst particle, wherein the solid wholly or almost wholly consists of metal. An example of a such an all-metal catalyst is a pellet of cobalt having a thin layer of cobalt oxide (CoO) on the exterior surface (resulting from oxidation of cobalt).

The decomposition of the alkylhydroperoxide in the oxidation mixture is effected with the aid of an above-described immobilized metal complex. The decomposition catalyst may be applied in a variety of ways. For instance, since the catalyst is immobilized on a carrier material, slurry reactors or packed beds can be used for converting the alkylhydroperoxide. The heat of reaction released in the exothermic decomposition reaction must be adequately collected and carried off to ensure good temperature control of the process. In particular, heat removal is readily accomplished when slurry reactors are used. Use of slurry reactors also allows for the desired temperature to be maintained during the decomposition by applying, for instance, reflux cooling. The continuous removal of heat obviates the need to recirculate evaporated products, consequently producing a somewhat favorable effect on the desired product yield. In such a situation, the amount of decomposition catalyst to be applied is, for instance, from 5 to 250 ppm metal in reference to the oxidation mixture. Preferably, an amount of from 10 to 150 ppm is applied.

The process can also be advantageously carried out in a packed-bed reactor because of the relatively high catalyst concentration reached therein. The packed-bed reactor is particularly advantageous when alkylhydroperoxide mixtures with a relatively low concentration are used. The water phase and the oxidation mixture may be passed through the reactor in the same direction of flow (co-current) or in opposite directions of flow (counter-current). A counter-current column (e.g., a rotating disc contactor) is preferred because it enables the highest base concentration (high pH) to be attained, allowing for the rapid decomposition and high conversion of alkylhydroperoxide.

If applied in a packed bed, the catalyst particles that make up the decomposition catalyst should possess respective diameters larger than 0.5 mm. Otherwise the pressure drop across the reactor will be too high. Preferably, the diameters are between 0.7 and 3 mm. The catalyst particles may be of any desired shape, including, by way of example, spherules, bars and granules.

The temperature during the decomposition step generally is in a range of from about 25 to about 200° C., and preferably is from about 50 to about 120° C. It is desirable to work at a temperature below which the non-catalyzed, thermal decomposition of the alkylhydroperoxide will occur. As explained above, conversion of the alkylhydroperoxide occurs by either catalyzed decomposition or thermal decomposition. However, the conversion preferably takes place by the catalyzed decomposition as opposed to thermal decomposition, since a higher selectivity of desired products is thereby obtained.

The decomposition can be effected in the presence of oxygen to attain a higher alkanone/alkanol (K/A) ratio. The rate of products produced by the decomposition step depends in part on the concentration of the transition metal on the carrier, the concentration of hydroperoxide, and the temperature. The decomposition step typically requires a residence time of between 5 and 300 minutes, and preferably between 15 and 120 minutes, although the residence time is not critical. Those skilled in the art can establish through simple analyses whether any alkylhydroperoxide remains in a treated mixture.

Upon completion of the decomposition step, the water phase can readily be separated from the decomposition mixture by, for instance, phase separation. Unreacted alkane and/or alkene and undesired side products can be removed by further processing. The separated water phase can be partly reused in a subsequent decomposition as earlier described herein; otherwise the separated aqueous solution is disposed of. This waste stream largely consists of alkali metal salts of inorganic and/or organic acids.

The addition of a basic aqueous solution may optionally be combined with a water wash and/or a neutralization step wherein acids contained in the oxidation mixture are first neutralized to form a neutralized organic phase containing the alkylhydroperoxide.

FIG. 1 is a schematic representation of the decomposition step in accordance with an embodiment of the present invention. The oxidation mixture obtained from the oxidation step is supplied through stream (1) to an optional neutralization step A. There, the oxidation mixture is treated with, for instance, an aqueous alkali metal hydroxide or alkali metal carbonate solution supplied through stream (5). The carboxylic acids formed during the alkane oxidation step are thereby partially removed and/or neutralized. The water phase in step A can be discharged in whole or in part through stream (6). Any water phase remaining in the oxidation mixture in step A can either in its entirety or with the addition of fresh basic aqueous solution supplied through stream (7) form the separate water phase. Subsequently, the oxidation mixture and water phase are supplied to the decomposition step B through stream (2). The water phase is then discharged from the decomposition step B and supplied by stream (3) to separation step C, where the water phase is separated from the oxidation mixture by phase separation. The water phase is discharged through stream (8). A portion of the water phase is preferably reused and recirculated through stream (9) to stream (2) and/or to stream (5) through stream (10). The alkanone/alkanol product mixture exits through stream (4). The oxidation mixture may optionally be subjected to a water wash before and after the above decomposition step and pretreatment step.

Figure 2:
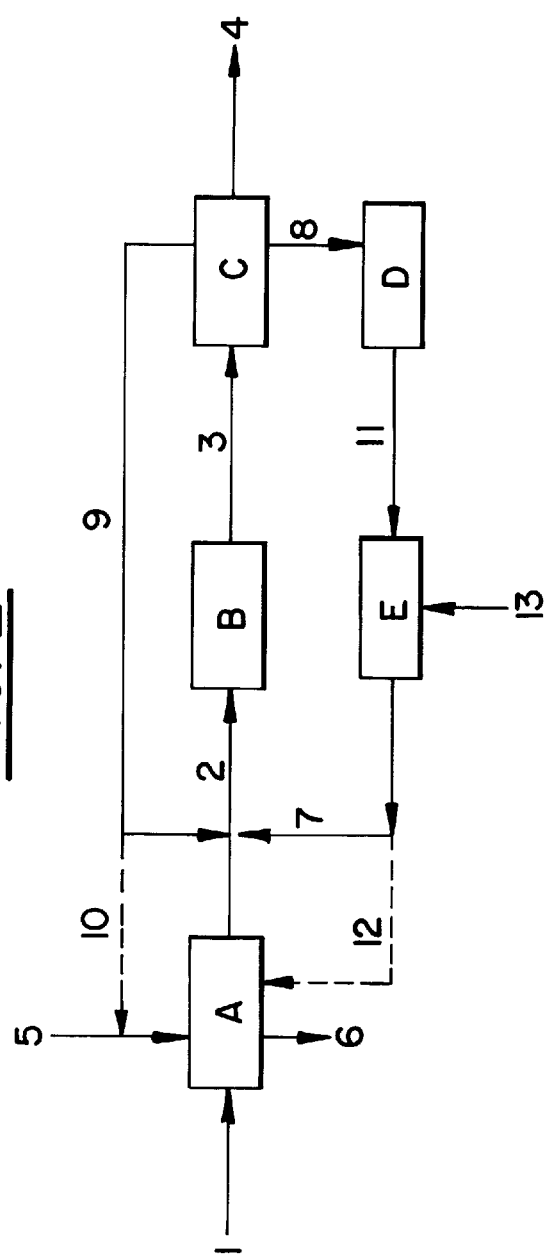
FIG. 2 is a schematic view representing a suitable process configuration for practicing the present invention according to a second preferred embodiment.

FIG. 2 is a schematic representation of another embodiment of the present invention, wherein the decomposition step according to FIG. 1 is modified such that the alkali metal carbonate or alkali metal hydroxide is reused by combusting the discharged water phases as described hereinabove. The water phase is discharged to the combustion installation D through stream (8). The alkali metal carbonate that forms here is discharged through stream (11) and is subsequently dissolved in water (supplied through stream (13)). The basic aqueous solution so obtained may subsequently be recirculated through stream (7) to stream (2) and/or through stream (12) to the optional neutralization step A.

After separation of the water phase, the organic phase can be further processed by distillation to thereby recover alkanol and alkanone, as well as unreacted alkane which can be returned to the oxidation reaction.

The following examples are provided in order to more fully illustrate the present invention, but are not to be construed as limiting the scope thereof.

EXAMPLES

The selectivity for cycloalkanol and cycloalkanone is calculated by dividing the sum of the cycloalkanol and cycloalkanone formed as a result of the decomposition step by the amount of cycloalkylhydroperoxide converted during the decomposition step (amounts provided in molar units).

Example I

The Preparation of Type A Catalyst

An aqueous solution of ammonium cobalt (II) EDTA (ethylene diamine tetraacetic acid) complex was prepared by dissolving $Co(NO_3)_2.6H_2O$ and EDTA at a molar ratio of 1/1 in water of high purity and then adding 25-wt. % $NH_3$ water solution so that ultimately the pH was equal to 9.0. The cobalt concentration of the resulting solution was 0.58 mol/L. This resulting solution was used for impregnating a $TiO_2$ carrier material having 10 g of $TiO_2$ extrudates (available from Norton Chemical Process Products Corporation; BET surface area 172 $m^2/g$, pore volume 0.31 $cm^3/g$, 3 mm cross-sectional area, length 1 cm). The carrier material was kept under vacuum for 10 minutes. Subsequently, 9.5 $cm^3$ of the cobalt solution was added to the carrier material while maintaining the vacuum. The amount of cobalt was sufficient for conducting full wetting of the carrier material. Next, the extrudates were vacuum-dried in successive one hour intervals at temperatures of 30° C., 50° C., 70° C., 90° C., and 100° C. Finally, the catalyst particles were calcined in an electric furnace for 4 hours at a maximum temperature of 500° C., the temperature in the oven being increased in increments of 1° C. per minute.

The resulting calcined catalyst was brown. Some catalyst granules were crushed to reveal fragments that also appeared to be brown, which is indicative of a homogeneous cobalt distribution.

The cobalt content was determined through neutron activation analysis (NAA) to be 2.6 wt. %.

Example II

The Preparation of Additional Type A Catalysts

Example I was repeated for preparing several other catalysts. The compositions of the catalysts are listed below in Table I.

TABLE I

| Type | Carrier | Metal | Metal content (wt. %) |
|------|---------|-------|----------------------|
| A | $TiO_2$ | Co | 2.6 |
| B | $ZrO_2$ | Co | 1.1 |
| C | $TiO_2$ | Fe | 3.5 |
| D | $TiO_2$ | Cu | 3.0 |
| E | $TiO_2$ | Ni | 2.5 |
| F | $TiO_2$ | Mn | 1.9 |

Batch Experiments

Example III 9.9 g of a water phase in which $Na_2CO_3$ (750 mmol $Na_2Co_3$/kg) was dissolved was added at room temperature to 99 g of a cyclohexane oxidation mixture containing 200 mmol cyclohexylhydroperoxide (CHHP) per kilogram, 60 mmol cyclohexanol (OL) per kilogram, and 30 mmol cyclohexanone per kilogram.

The resulting mixture was heated to a temperature of 73° C., whereupon 0.626 g of a Type A catalyst prepared in accordance with Example I was added. The decomposition of CHHP was monitored by means of iodometric titration. The first-order rate constant was $4.2*10^{-4}$ kg solution/(g cat*min). The selectivity for cyclohexanol plus cyclohexanone was 103.3%. The molar cyclohexanol/cyclohexanone ratio was 0.74.

Example IV

Example III was repeated with the exception that 49 g of a water phase in which $Na_2CO_3$ (750 mmol $Na_2CO_3$/kg water) was dissolved was used. This mixture was heated to a temperature of 73° C., whereupon 0.68 g of a Type A catalyst was added. The decomposition of the CHHP was monitored by means of iodometric titration. The first-order rate constant was $9.5*10^{-4}$ kg solution/(g cat*min). The selectivity for cyclohexanol plus cyclohexanone was 100.6%. The molar cyclohexanol/cyclohexanone ratio was 0.64.

Example V

Example III was repeated with the exception that 200 g of water phase in which $Na_2CO_3$ (750 mmol/kg) was dissolved was used. This mixture was heated to a temperature of 73° C., whereupon 0.64 g of catalyst (Type A) was added. The decomposition of the CHHP was monitored by means of iodometric titration. The first-order rate constant was $22.6*10^{-4}$ kg solution/(g cat*min).

Example VI

Example III was repeated with the exception that 10.4 g of water phase in which $Na_2CO_3$ (2000 mmol/kg) was dissolved was used. This mixture was heated to a temperature of 73° C., whereupon 0.60 g of Type A catalyst was added. The decomposition of the CHHP was monitored by means of iodometric titration. The first-order rate constant was $13.0*10^{-4}$ kg solution/(g cat*min). The selectivity for cyclohexanol plus cyclohexanone was 97.3%. The molar cyclohexanol/cyclohexanone ratio was 0.71.

Example VII

Example III was repeated with the exception that 11.0 g of water phase in which $Na_2CO_3$ (1000 mmol/kg) was dissolved was used. This mixture was heated to a temperature of 73° C., whereupon 0.64 g of a Type B catalyst prepared in accordance with Example II was added. The decomposition of the CHHP was monitored by means of iodometric titration. The first-order rate constant was $10.2*10^{-4}$ kg solution/(g cat*min). The selectivity for cyclohexanol plus cyclohexanone was 100.3%. The molar cyclohexanol/cyclohexanone ratio was 0.74.

Example VIII

Example III was repeated with the exception that 11.2 g of water phase in which $Na_2CO_3$ (1000 mmol/kg) was dissolved was used. This mixture was heated to a temperature of 73° C., whereupon 0.64 g of a Type C catalyst prepared in accordance with Example II was added. The decomposition of the CHHP was monitored by means of iodometric titration. The first-order rate constant was $1.25*10^{-4}$ kg solution/(g cat*min).

Example IX

Example III was repeated with the exception that 11.2 g of water phase in which $Na_2CO_3$ (1000 mmol/kg) was dissolved was used. This mixture was heated to a temperature of 73° C., whereupon 0.84 g of a Type D catalyst prepared in accordance with Example II was added. The decomposition of the CHHP was monitored by means of iodometric titration. The first-order rate constant was $2.02*10^{-4}$ kg solution/(g cat*min).

Example X

Example III was repeated with the exception that 10.2 g of water phase in which $Na_2CO_3$ (1000 mmol/kg) was dissolved was used. This mixture was heated to a temperature of 73° C., whereupon 0.98 g of a Type E catalyst prepared in accordance with Example II was added. The decomposition of the CHHP was monitored by means of iodometric titration. The first-order rate constant was $1.2*10^{-4}$ kg solution/(g cat*min).

Example XI

Example III was repeated with the exception that 10.4 g of water phase in which $Na_2CO_3$ (1000 mmol/kg) was dissolved was used. This mixture was heated to a temperature of 73° C., whereupon 0.97 g of a Type F catalyst prepared in accordance with Example II was added. The decomposition of the CHHP was monitored by means of iodometric titration. The first-order rate constant was $1.6*10^{-4}$ kg solution/(g cat*min).

Example XII

Example III was repeated with the exception that 78 g of water phase in which $Na_2CO_3$ (1000 mmol/kg) was dissolved was used. This mixture was heated to a temperature of 73° C., whereupon 0.82 g of an all-cobalt catalyst (pellets 5 mm in diameter) was added. The decomposition of the CHHP was monitored by means of iodometric titration. The first-order rate constant was $8.5*10^{-4}$ kg solution/(g cat*min).

Example XIII

Example III was repeated with the exception that 10.2 g of water phase in which $Na_2CO_3$ (750 mmol/kg) was dissolved was used. This mixture was heated to a temperature of 73° C., whereupon 0.84 g of pelletized $CoCO_3$ (pellets 1 cm in diameter) was added. The decomposition of the CHHP was monitored by means of iodometric titration. The first-order rate constant was $46.2*10^{-4}$ kg solution/(g cat*min).

Example XIV

Example III was repeated with the exception that 10.4 g of water phase in which NaOH (2000 mmol/kg) was dissolved was used. This mixture was heated to a temperature of 73° C., whereupon 0.64 g of a Type A catalyst was added. The decomposition of the CHHP was monitored by means of iodometric titration. The first-order rate constant was $15.7*10^{-4}$ kg solution/(g cat*min).

Example XV

Example III was repeated with the exception that 10.4 g of water phase in which $K_2CO_3$ (1000 mmol/kg) was dissolved was used. This mixture was heated to a temperature of 73° C., whereupon 0.77 g of a modified Type A catalyst containing 1.4 wt. % Co was added. The decomposition of the CHHP was monitored by means of iodometric titration. The first-order rate constant was $11.0*10^{-4}$ kg solution/(g cat*min).

Example XVI

Example III was repeated with the exception that 10 g of water phase in which RbOH (1000 mmol/kg) was dissolved was used. This mixture was heated to a temperature of 73° C., whereupon 0.64 g of catalyst was added. The decomposition of the CHHP was monitored by means of iodometric titration. The first-order rate constant was $20.4*10^{-4}$ kg solution/(g cat*min).

Comparative Experiment A

Example III was repeated with the exception that no water phase was added. On heating to a temperature of 73° C., 1.1 g of a Type A catalyst was added. The decomposition of CHHP was monitored by means of iodometric titration. The first-order rate constant was $0.6*10^{-4}$ kg solution/(g cat*min).

Example XVII 12 g of a water phase in which $Na_2CO_3$ (750 mmol/kg) was dissolved was added at room temperature to 100 g of a cyclododecane oxidation mixture containing 400 mmol cyclododecyl hydroperoxide (CDHP) per kilogram, 70 mmol cyclododecanol (DOL) per kilogram, and 40 mmol cyclododecanone (DON) per kilogram. This mixture was heated to a temperature of 73° C., whereupon 0.7 g of a Type A catalyst with 2.4% Co was added. The decomposition of the CHHP was monitored by means of iodometric titration. The first-order rate constant was $3.6*10^{-4}$ kg solution/(g cat*min). The selectivity for DOL plus DON was 106.2%. The molar DOL/DON ratio was 0.85.

Continuous Experiments

Example XVIII 6.0 g of a Type A catalyst was introduced into a hollow, glass container provided with slits of 1 mm. This container was placed in a 1-l continuous-flow reactor provided with baffles. 45 g per hour of an organic phase (i.e., cyclohexane oxidation mixture containing 200 mmol cyclohexylhydroperoxide (CHHP) per kilogram, 60 mmol cyclohexanol (OL) per kilogram and 30 mmol cyclohexanone (ONE) per kilogram) and 13 g of a water phase in which $Na_2CO_3$ (1000 mmol/kg) was dissolved was added using two pumps. The two phases were mixed in the reactor with the aid of a turbine stirrer operating at 1400 revolutions per min. The reaction temperature was 69° C. Any evaporating liquid was returned to the reactor by way of a reflux condenser. The liquid that overflowed was collected in a 5-l vessel. The conversion of the CHHP was determined by means of iodometric titration of this overflowing liquid. By operating this system in the manner herein described, a CHHP conversion of 40% was achieved over a period of 1000 hours. The conversion could be varied by varying the residence time, the amount of catalyst, the concentration of the base, and the ratio of the water phase to the organic phase. The measured Co concentration in the effluent was less than 2 ppb.

Comparative Experiment B

Example XVIII was repeated with the exception that only water was used in the water phase. Acids, which were present in the organic phase or otherwise formed, were consequently extracted towards the water phase, causing the pH in the water phase to drop below 7. The catalyst was completely deactivated within 24 hours.

Comparative Experiment C

Comparative experiment B was repeated with the exception that the catalyst was made of an aminosilane modified silica to which a Co salt was linked as described in Example XXVIII of WO/9216487. The catalyst was completely deactivated within 24 hours.

Example XIX 15 g of a Type B catalyst were introduced into hollow, glass containers provided with slits of 1 mm. These containers were placed in a 1-l continuous-flow reactor provided with baffles. 45 g per hour of an organic phase (i.e., a cyclododecane oxidation mixture containing 400 mmol cyclododecylhydroperoxide (CDHP) per kilogram, 70 mmol cyclododecanol (DOL) per kilogram, and 40 mmol cyclododecanone (DON) per kilogram) and 13 g of a water phase in which $Na_2CO_3$ (1000 mmol/kg) was dissolved was added using two pumps. The two phases were mixed in the reactor with the aid of a turbine stirrer (1400 revolutions per min). The reaction temperature was 89° C. Any evaporating liquid was returned to the reactor by way of a heated reflux condenser. The liquid that overflowed was collected in a 5-l vessel. The conversion of the CHHP was determined by iodometric titration of this overflowing liquid. By operating this system in the manner as described, a CDHP conversion of 80% was achieved over a period of 500 hours. The conversion could be varied by varying the residence time, the amount of catalyst, the concentration of the base, and the ratio of the water phase to the organic phase. The measured Co concentration in the effluent was less than 1 ppb.

A process for decomposing an alkylhydroperoxide is disclosed in BE-A-09301446, filed Dec. 23, 1993, the complete disclosure of which is incorporated herein by reference.

Although the present invention has been described in detail with reference to its presently preferred embodiments, it will be understood by those of ordinary skill in the art that various modifications and improvements to the present invention are believed to be apparent to one skilled in the art. Accordingly, no limitation upon the invention is intended, except as set forth in the appended claims.

What is claimed is:

1. A process for preparing an alkanone an alkanol, or a mixture thereof comprising the steps of:
    oxidizing an alkane having from 3 to 30 carbon atoms, an alkene having from 3 to 30 carbon atoms, or a mixture thereof with oxygen to form an oxidation mixture containing alkylhydroperoxide;
    combining a basic, aqueous solution with said oxidation mixture to form a separate basic water phase having a pH higher than 8.5; and
    decomposing said alkylhydroperoxide in the presence of a catalyst under reaction conditions effective for the formation of said alkanone, alkanol, or mixture thereof, wherein said catalyst comprises a metal oxide or metal oxide forming compound immobilized on a inorganic carrier material which is selected from the group consisting of $TiO_2$, $ZrO_2$, $MnO_2$ and carbon.

2. A method as recited in claim 1, wherein the metal in said metal oxide forming compound or said metal oxide is selected from the group consisting of Mn, Fe, Co, Ni, and Cu.

3. A process as recited in claim 2, wherein the weight percentage of said metal relative to said carrier material is between 0.2 and 4 wt. %.

4. A process as recited in claim 2, wherein said basic aqueous solution is at least one base selected from the group consisting of alkali metal hydroxide, alkali metal carbonate, and alkali metal phosphate.

5. A process as recited in claim 4, wherein the weight ratio of oxidation mixture to water phase is between 100:1 and 1:1.

6. A process as recited in claim 2 or 4, wherein said water phase has a pH higher than 8.5 at 25° C.

7. A process as recited in claim 2 or 4, wherein said water phase has a pH higher than 9 at 25° C.

8. A process as recited in claim 2 or 4, wherein said water phase has a pH between 10 and 11 at 25° C.

9. A process as recited in claim 2, wherein said step of decomposing said alkylhydroperoxide is effected in a packed-bed reactor and wherein said catalyst consists of particles with a particle size of between 0.7 and 3 mm.

10. A process as recited in claim 2, wherein said alkane is a cycloalkane having from 6 to 12 carbon atoms.

11. A process as recited in claim 10, wherein said cycloalkane is a cyclohexane.

12. A process as recited in claim 2 or 5, wherein said basic aqueous solution contains dissolved sodium carbonate.

13. A process as recited in claim 2, which is a continuous process in which said process further comprises the steps of:
    continuously extracting said basic water phase after said step of decomposing said alkylhydroperoxide; and
    partly recirculating said extracted water phase to the decomposition step.

14. A process as recited in claim 2, which is a continuous process wherein said basic, aqueous solution is of an alkali metal carbonate, which continuous process comprises the further steps of:
    continuously extracting said basic water phase after said step of decomposing said alkylhydroperoxide;
    combusting said extracted water phase after said decomposition step at a temperature of from 550° to 1200° C. to obtain alkali metal carbonate;
    preparing a further amount of basic, aqueous solution, said further basic, aqueous solution being of said alkali metal carbonate; and
    recycling said further basic, aqueous solution to said decomposition step.

15. A process as recited in claim 13, wherein the metal in said metal compound is selected from the group consisting of Mn, Fe, Co, Ni, and Cu, said carrier material is inorganic and stable in the presence of said separate basic water phase, wherein said basic, aqueous solution the base is selected from the group consisting of alkali metal hydroxide, alkali metal carbonate, alkali metal phosphate, and a combination of any thereof, and wherein said water phase has a pH higher than 8.5 at 25° C.

16. A process as recited in claim 15, wherein said alkane is a cycloalkane having from 6 to 12 carbon atoms.

17. The process according to claim 1, wherein said oxidation is conducted at a temperature of about 120° C. to 200° C., at a pressure of between 0.4 Mpa and 5.0 Mpa.

18. The process according to claim 17, wherein the temperature is 140° C. to 180° C.

19. A process according to claim 1, wherein said oxidation step is conducted at 120° C. to 200° C., said decomposition step is conducted at 25° C. to 200° C., and the alkane and the alkene have 4 to 18 carbon atoms.

* * * * *